United States Patent [19]
Waitz et al.

[11] Patent Number: 5,688,246
[45] Date of Patent: *Nov. 18, 1997

[54] MICROCANNULA

[75] Inventors: Harold D. Waitz; Hal Sternberg; Paul E. Segall, all of Berkeley; Bruce Cohen, Albany, all of Calif.

[73] Assignee: BioTime, Inc., Berkeley, Calif.

[*] Notice: The term of this patent shall not extend beyond the expiration date of Pat. No. 5,484,417.

[21] Appl. No.: 547,618

[22] Filed: Oct. 24, 1995

Related U.S. Application Data

[63] Continuation-in-part of Ser. No. 348,743, Nov. 30, 1994, Pat. No. 5,484,417, which is a continuation of Ser. No. 237,826, May 4, 1994, abandoned, which is a continuation of Ser. No. 25,158, Mar. 1, 1993, abandoned, which is a continuation-in-part of Ser. No. 687,843, Apr. 19, 1991, abandoned.

[51] Int. Cl.⁶ .................................................. A61M 5/178
[52] U.S. Cl. .......................... 604/165; 604/264; 604/239; 604/274; 604/280
[58] Field of Search .................................... 604/264, 265, 604/164–168, 158, 239, 280, 272–274; 606/223

[56] References Cited

U.S. PATENT DOCUMENTS

| | | |
|---|---|---|
| 3,750,667 | 8/1973 | Pshenichny et al. |
| 3,783,876 | 1/1974 | Dye . |
| 3,788,119 | 1/1974 | Arrigo ......................... 604/274 X |
| 4,191,176 | 3/1980 | Spina ............................... 604/51 |
| 4,198,973 | 4/1980 | Millet ......................... 604/165 X |
| 4,411,657 | 10/1983 | Galindo ........................... 604/274 |
| 4,413,993 | 11/1983 | Guttman . |
| 4,565,545 | 1/1986 | Suzuki . |
| 4,588,398 | 5/1986 | Daugherty . |
| 4,808,156 | 2/1989 | Dean . |
| 4,808,170 | 2/1989 | Thornton et al. ............. 604/274 |
| 4,842,585 | 6/1989 | Witt . |
| 4,917,670 | 4/1990 | Hurley et al. . |
| 4,994,036 | 2/1991 | Biscoping et al. ............ 604/158 |
| 5,009,643 | 4/1991 | Reich et al. .................... 604/165 |
| 5,100,390 | 3/1992 | Lubeck et al. . |
| 5,261,891 | 11/1993 | Brinkerhoff et al. .......... 604/165 |
| 5,484,417 | 1/1996 | Waitz et al. .................... 604/264 |

OTHER PUBLICATIONS

French Gauge Conversion Chart.

*Primary Examiner*—Michael Powell Buiz
*Assistant Examiner*—Chalin Smith
*Attorney, Agent, or Firm*—Karl Bozicevic; Bret Field; Bozicevic & Reed

[57] ABSTRACT

A microcannula suitable for cannulation of very small blood vessels in a small animal, neonate or adult having a sharp pointed trochar tightly but removable placed in the lumen of the microcannula. The trochar is held in place by contact friction from an area of reduced inside diameter distal to the tip end, formed by welding the end distal of the microcannula to a tube having a slightly larger diameter. A process for making a microcannula.

12 Claims, 4 Drawing Sheets

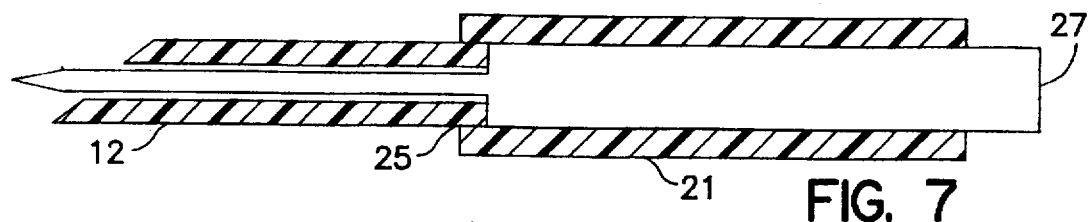
FIG. 7
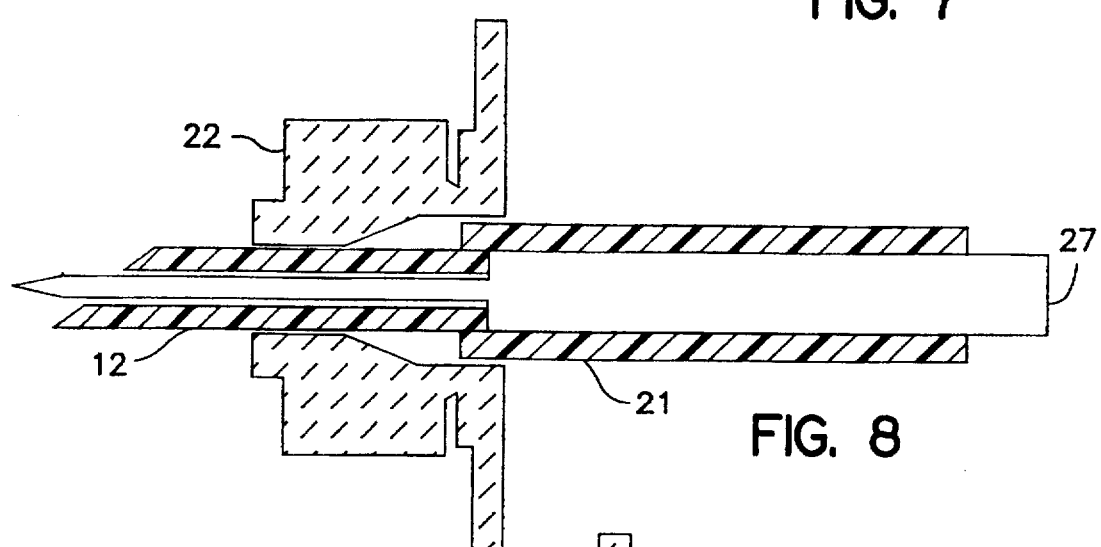
FIG. 8
FIG. 9
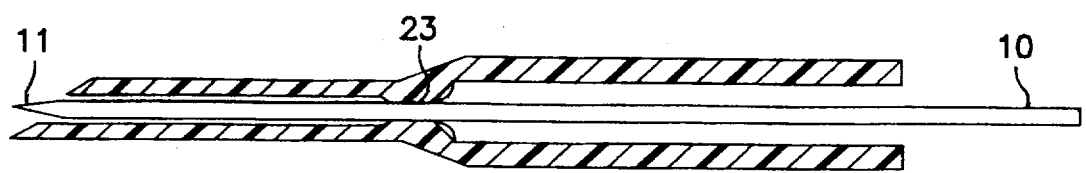
FIG. 10

MICROCANNULA

RELATED APPLICATIONS

This application is a continuation-in-part application of U.S. patent application Ser. No. 08/348,743, filed Nov. 30, 1994, now U. S. Pat. No. 5,484,417, which is a continuation of U.S. patent application Ser. No. 08/237,826, filed May 4, 1994, now abandoned, which is a continuation of U.S. patent application Ser. No. 08/025,158, filed Mar. 1, 1993, now abandoned, which is a continuation-in-part application of U.S. patent application Ser. No. 07/687,843, filed Apr. 19, 1991, now abandoned, which applications are incorporated herein by reference and to which applications we claim priority under 35 USC § 120.

BACKGROUND OF THE INVENTION

The present invention relates to the field of surgical devices, specifically cannulas.

Cannulas are hollow tube instruments used to deliver fluids to or remove fluids from blood vessels, ducts or other hollow organs of animals. While many sizes of cannulas are available commercially, microcannulas suitable for use in surgery on small animals are of limited design and utility. The smallest commercially available cannulas are generally flat tipped and are large enough to accommodate a 14 to 24 gauge needle in the lumen of the cannula, which needle is used as a trochar. Small cannulas are generally made of small bore polyethylene or PTFE tubing and usually require an incision to be made in the vessel being cannulated. They can be supplied with a hypodermic needle which is used to create an incision and to block the cannula to prevent fluid contained in the vessel of the hollow organ from draining until the cannula is in place in the vessel or other hollow organ.

As cannulas decrease in size, they become more flexible and easily bent, and therefore difficult to manipulate. The flexibility of small cannulas occurs because of the decreasing absolute wall thickness of the cannula as they get smaller in diameter, and concomitant loss of rigidity of the cannula wall.

Conventional cannulas are supplied with trochars that move freely in the lumen of the cannula since it is conventionally desirable to be able to quickly remove the trochar once a vessel is cannulated.

Conventional small cannulas appropriate for use in cannulation of small blood vessels in microsurgery are notoriously difficult to use. The smallest cannulas available frequently require many minutes of patient and skilled manipulation to prepare a micro-incision in a blood vessel and properly place the cannula in small blood vessels. Furthermore such small cannulas suitable for microsurgery are frequently supported by an outside surrounding heavy gauge needle or auxiliary tube and the microcannula is placed inside the supporting tube. One of the main disadvantages of this conventional arrangement of microcannula and surrounding-supporting tube is that the wound made by the larger supporting hollow tube is larger than that which would be required if the microcannula were more robust. Large incisions weaken the vessel wall and damage the vessel.

It would be useful to provide a cannula suitable for microcannulation of small blood vessels in animals such as mice with sufficient rigidity to be easily manipulated and which does not require a vessel incision larger than the microcannula.

SUMMARY OF THE INVENTION

The present invention features a microcannula having a very small bore tube with a beveled tip and a sharp pointed trochar tightly but removably placed in the lumen of the small bore tube. This microcannula has sufficient rigidity to be relatively easily manipulated. Furthermore by means of using a sharp pointed trochar and bevel tipped tube, it is possible to cannulate a small blood vessel without the necessity of incising the blood vessel wall before inserting the cannula and trochar. The microcannula of the invention is also provided with a segment having an expanded outer diameter distal to the beveled tip of the microcannula useful for securing the cannula in a blood vessel or other hollow anatomical structure, as is described herein below.

It is an object of the invention to provide an easily manipulated microcannula which can be used to cannulate small hollow organs and blood vessels in a short period of time with a minimum of blood loss.

It is yet another object of the invention to provide a microcannula and trochar that can be used to cannulate a blood vessel without making a preparatory incision before inserting the trochar and cannula into the blood vessel.

It is still another object of the invention to provide a microcannula that can be easily secured in the cannulated blood vessel or other hollow anatomical structure.

In one embodiment of the microcannula of the invention, the microcannula is adapted to use with fluid supply systems such as syringes and pumps by being welded at the end distal to the tip to a tube having a larger diameter than that of the microcannula. The microcannula tube and the larger tube are welded together such that an area of reduced inside diameter at the weld site is produced at a site distal to the tip. The area of reduced diameter provides friction contact with the solid trochar such that the trochar is immobilized during insertion of the microcannula unit into a blood vessel.

In one aspect, the invention provides a process of producing a microcannula having an area of reduced inside diameter distal to the tip and which is adapted for use with supply systems such as syringes and pumps.

These and other objects, advantages such as ease of manipulation, and features such as an outside diameter of about 0.016 inch of the present invention will become apparent to those persons skilled in the art upon reading the details of the microcannula and process of producing the microcannula as more fully set forth below.

BRIEF DESCRIPTION OF THE FIGURES

FIG. 7 shows a first step in the process of producing a microcannula adapted for use with fluid supply systems having an area of reduced diameter in which smaller and larger diameter tubes are aligned on a mandrel.

FIG. 8 shows a second step in the process of producing a microcannula adapted for use with fluid supply systems having an area of reduced diameter in which the tube-mandrel assembly is placed in a welding die.

FIG. 9 shows a third step in the process of producing a microcannula adapted for use with fluid supply systems having an area of reduced diameter in which a weld is formed.

FIG. 10 shows an embodiment of the microcannula of the invention adapted for use with fluid supply systems and having an area of reduced inside diameter which provides friction contact to removably hold the trochar.

DETAILED DESCRIPTION

Before the present microcannula and method of producing the microcannula are described, it is to be understood that this invention is not limited to the particular microcannulas, materials, or processes described as such microcannulas, materials, or processes may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an", and "the" include plural references unless the context clearly dictates otherwise. Thus, for example, reference to "a process" includes one or more steps of the type described herein and/or which will become apparent to those persons skilled in the art upon reading this disclosure.

In greater detail, the microcannula according to the invention comprises a hollow tube 12 (FIG. 3) having a cross sectional size smaller that a 24 gauge needle and larger than a 29 gauge needle. More precisely the outside diameter of the body of the microcannula 12 is about 0.016 inch. The outside diameter of the tubing will vary slightly, but in general the outside diameter of the tube will be between about 0.018 and 0.014 inches. Usually the outside diameter of the tubing will be 0.016±0.001".

The inside diameter of the body of the microcannula is about 0.008 inch. The inside diameter of the tubing will vary slightly, but in general the inside diameter of the tube will be on a range between about 0.010 and 0.006 inches. Usually the inside diameter of the tubing will be 0.008"±0.001".

Figure 2:
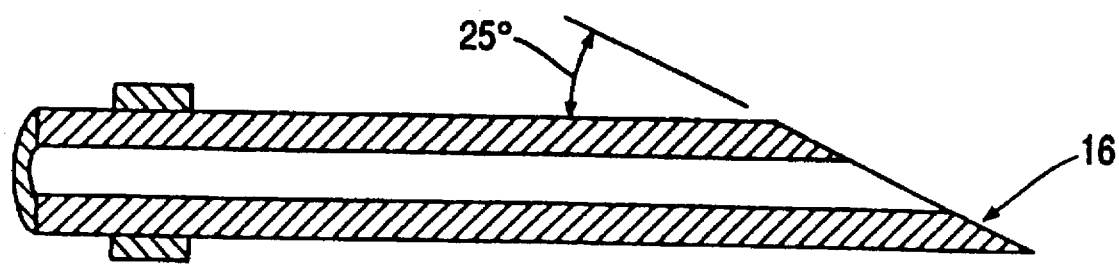
FIG. 2 is a cross-section of the microcannula according to the invention.
Figure 3:
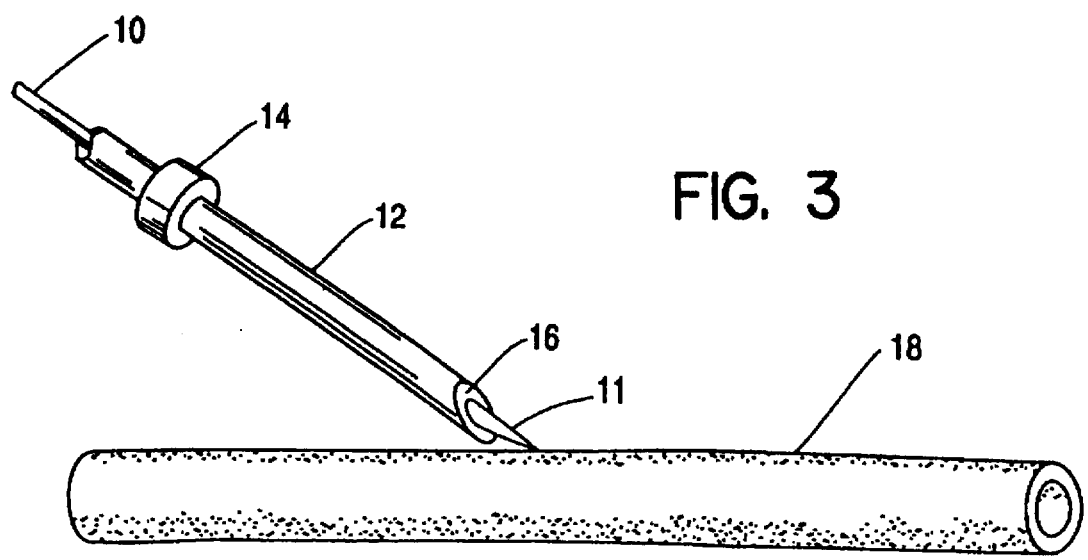
FIG. 3 shows the trochar and microcannula in use as a unit just prior to penetration of a blood vessel wall or other hollow tube by the point of the trochar.

The microcannula according to the invention will have a simple beveled tip 16 (FIGS. 2 and 3). The angle of the beveled tip is about 25°. The angle of the bevel may vary in a range between 23° and 27°, but the best performance of the microcannula is achieved when the bevel is 25°±0.50°. The angle of the microcannula tip is measured with respect to one side of the microcannula tube as is shown in FIG. 2.

The microcannula of the invention will generally be made of bio-compatible polymer tubing. It is preferred that the biocompatible polymer be perfluorocarbon material.

The microcannula described above is highly flexible and delicate and is difficult to insert into the lumen of a blood vessel or other hollow organ requiring cannulation. In order to facilitate manipulation of the microcannula, a solid trochar 10 is provided for use with the microcannula (FIG. 3). The trochar 10 fits in the lumen of the microcannula tube and may be removed therefrom. It is preferred that the trochar be of a size that fits tightly in the lumen of the microcannula tube and does not move freely in the lumen; however, the trochar must also be small enough to be removed from the lumen of the microcannula when the side of the microcannula is grasped and held and the trochar is pushed or pulled from the lumen of the tube. The preferred performance of the trochar is best obtained when the outside diameter of the trochar is slightly smaller than the inside diameter of the tube.

Figure 6A:
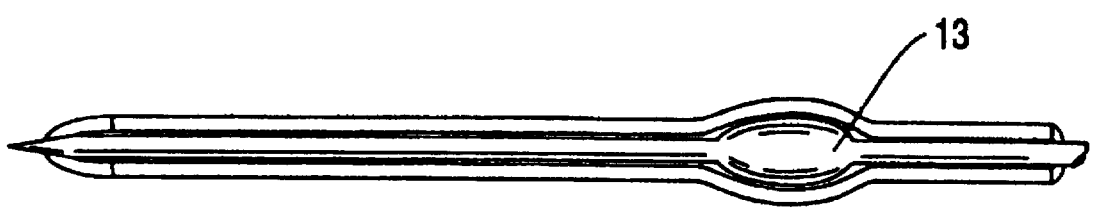
FIG. 6a–b shows top and side views of the trochar of FIG. 1 with the flattened segment distal to the pointed tip of the trochar which provides contact with the inner walls of the lumen of the microcannula.
Figure 6B:
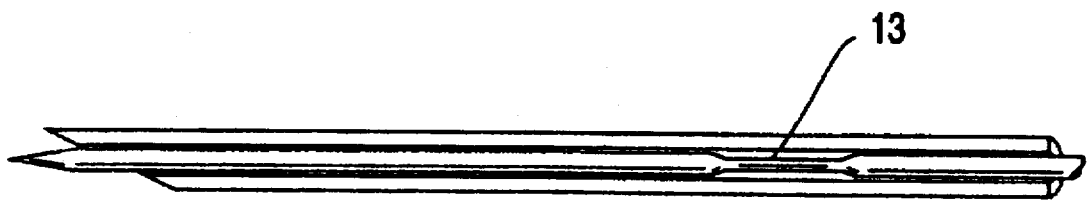

In one preferred embodiment, a portion of the length of the trochar will be expanded in width to provide contact with the inner walls of the lumen of the microcannula (FIG. 6). This contact provides friction with the inner wall of the microcannula. This friction holds the trochar in the microcannula tube when the tip of the trochar and microcannula contact, pierce and advance into the blood vessel or other hollow anatomical structure to be cannulated. In a preferred embodiment the expanded in width portion of the length of the trochar will be provided by a flattened or swedged segment 13 of the trochar which is wider than the average diameter of the wire from which the trochar is formed (FIG. 6).

The flattened or swedged segment 13 of the trochar is generally found distal to the pointed tip 11 of the trochar, wherein the distal direction is the direction away from the tip of the trochar. While the flattened or swedged segment 13 is located at any point distal to the tip of the trochar and may be provided at any point on the length of the trochar, it is preferred to limit the flattened or swedged portion to a segment which fits into the distal end of the microcannula when the trochar is inserted within the lumen of the microcannula with the tip of the trochar extending beyond the tip of the microcannula.

Although it is possible to provide a wire that has a spline or edge or is extruded in an oval cross section, wherein the spline, edge or portion of the oval cross-section wire would contact the inside of the wall of the tube forming the microcannula, it is preferred that the length of the swedged or flattened segment is only a small portion of the length of the trochar. For microcannulas according to the invention it is preferred that the swedged portion not exceed 5 mm in length. In general the swedged portion will not be shorter than the diameter of the wire from which the trochar is formed. Preferably, the length of the swedged portion will be 1.25 to 4 times the diameter of the wire from which the trochar is formed.

In more detail, and as a non-limiting example of a preferred embodiment, the trochar is formed of a substantially round wire having a diameter of about 0.008". The swedged segment will consist of a flattened area which is about 0.016" wide in its widest dimension measured perpendicular to axis of the length of the wire and about 0.024" in length measured with the axis of the length of the wire. In general, if the round wire has an average diameter 0.008", the width of the swedged segment will be in a range between 0.019" and 0.015".

The swedged segment resulting from the flattening process which is described herein below, will generally be thinner than the average diameter of the wire when measured in the plane perpendicular to the widest dimension of the swedged segment. Thus, for example in a preferred embodiment, the thickness of the swedged segment of an average diameter 0.008" wire will be about 0.004". This dimension will have a range between 0.003" and 0.005" when the trochar is made from a 0.008" wire.

The shape of the swedged segment of the trochar may also vary. The shape may be oval, circular or even square depending upon the method used to produce the swedged segment. Thus, for example, the swedged portion of the trochar may be produced by pinching the wire between rollers which are set to have a space between the rollers which is smaller than the diameter of the wire from which the trochar is formed. Alternatively the wire may be extruded with a variable diameter over a short segment of the wire, thus providing a thickened aspect over some distance of the wire.

It is preferred to produce the swedged segment in the wire from which the trochar is formed by striking the wire between symmetrical dies. The surface of the dies are shaped to produce the swedged segment in the wire when the wire is pressed between the dies. In a preferred embodiment, the dies will produce a swedged region which is narrower at one end and increases in width toward the opposite end before quickly ending. The shape of the swedged segment is in this preferred embodiment, spade shaped, with the narrow end of the spade shaped swedged segment closer to the point of the trochar.

Figure 1:
FIG. 1 is a side view of the trochar according to the invention.

The trochar used with the cannula is conically pointed. The interior angle of the point of said trochar, when measured as is illustrated in FIG. 1, may vary between about 35° and 5° depending upon the sharpness of the point desired. A sharp point may be desired if the trochar must pierce a robust or fibrous tissue. For such sharp points, an angle of about 8° is preferred and the length of the point of the trochar is about six times the diameter of said trochar. Lengths substantially greater that about six times the diameter of the trochar lead to undesirable delicate points that can flex and break. Therefore, it is preferred that the length of a sharp trochar point is about six times the diameter of the trochar or less.

With respect to the cannulation of small delicate hollow anatomical structures such as a duct or small blood vessel of a subject, or even a major blood vessel of a very small experimental animal, or neonate of any species, the trochar used with the microcannula will have a conical point that is less acute in angle. The trochar point will have an angle in a range between about 20° and 35°. Points having an angle between about 25° and 30° have been found in practice to be particularly easy to handle when cannulating small blood vessels. A trochar tip angle of about 28° is most preferred.

The trochar may be made of any strong wire stock. It is preferred that the wire is not of a ductile metal since the trochar confers rigidity to the microcannula when it is inserted into the lumen thereof. Furthermore ductile wires cannot be easily inserted into the lumen of the microcannula with the required tight fit without bending or breaking. It is preferred that the trochar is made of stainless steel.

The microcannula of the invention further comprises a segment of the microcannula tube that has an expanded outside diameter and is located distal to the tip of the microcannula. The expanded outside diameter of shoulder 14 (FIG. 3) may be in the form of a ring of tubing or an "O" ring adhered to the outside wall of the microcannula tube, dried plastic glue or a thickening in the wall of the microcannula itself.

In a preferred embodiment, the expanded outside diameter of the shoulder 14, as indicated above, is provided by a ring of tubing which fits tightly around the outside wall of the microcannula tube 12, but which may be moved if desired to various positions thereon. The advantage gained by a movable ring is that the microcannula may be secured in the cannulated vessel at any desired depth of the tip of the microcannula in the vessel. Thus, if a deep cannulation is desired, with the tip of the microcannula advanced far into the cannulated anatomical structure or vessel, the ring forming the shoulder 14 may be moved distally away from the microcannula tip to allow a deep penetration of the microcannula tip prior to securing the microcannula tube 12 with the ligature 20 tied around the vessel 18 on one end and the microcannula tube 12 behind the shoulder 14 as is shown in FIG. 5.

As was mentioned above, the shoulder 14 may be provided by a movable ring in the form of a small piece of tubing. Equally, the ring may be an "O" ring or other annular structure. It is preferred that the internal diameter of the tightly fitted movable ring will be sightly smaller that the outside diameter of the hollow tube 12 forming the microcannula. In general, the inside diameter of the movable ring and the outside diameter of the microcannula will be chosen so as to establish an interference fit, in which the internal diameter of the movable ring is slightly smaller than the outside diameter of the wall of the tube 12 forming the microcannula. An interference fit in a range of about 0.0015" to 0.0005" will be selected; an interference fit of about 0.001" is preferred.

Figure 5:
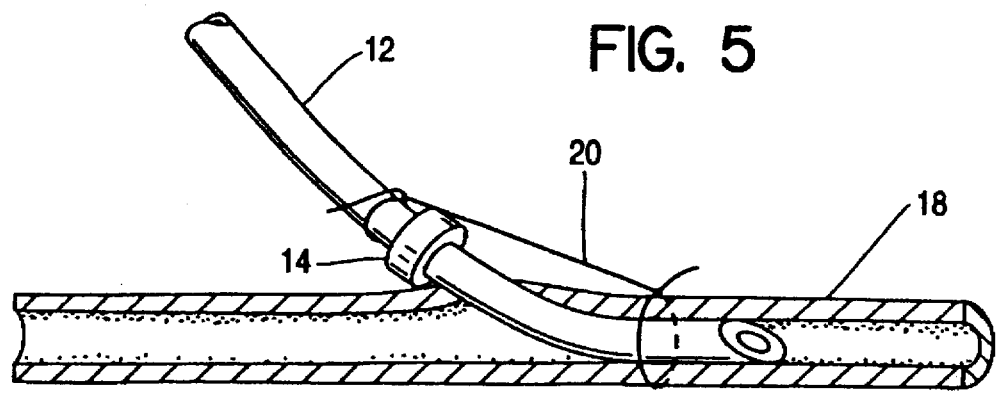
FIG. 5 shows the microcannula in place in a blood vessel or other hollow tube with the blood vessel tied off around the proximal end of the microcannula and the microcannula secured in place.

In general, the movable ring will have an outside diameter large enough to provide a usable stop for securing the ligature 20 as shown in FIG. 5. An outside diameter of at least two to three times the inside diameter of the movable ring is preferred. If the inside diameter of the ring is particularly small, the outside diameter of the ring will be larger than two times the inside diameter. In a preferred embodiment, the tube 12 of the microcannula has an outside diameter of 0.016" and the movable ring has an inside diameter of 0.015" and an outside diameter of 0.043".

It is preferred that the movable ring be made of a material which will stretch sufficiently to allow it to be fitted over the outside wall of the microcannula tube 12; however, if the material comprising the microcannula tube is resilient and may be slightly compressed without substantially closing the lumen of the microcannula tube 12, the movable ring can be made of a more rigid material such as a metal.

When in use, the shoulder 14 is used to secure the distal end of the microcannula using a ligature 20, one end of which is tied around the distal end of the microcannula and the other end of which is tied around the blood vessel 18 surrounding the end of the microcannula proximal to the beveled tip, as depicted in FIG. 5, or it may be secured to surrounding tissue.

The distal end of the microcannula, which is the end of the microcannula away from the beveled tip, is secured within the lumen of a larger tube which may in turn be secured to the tip of a needle or still larger piece of tubing such as a small commercially available catheter, e.g., an angiocath. The distal end of the microcannula can in this fashion be conveniently connected to conventional fittings for tubing or syringes such as luer lock fittings and the like.

Tubing of the type used to make the microcannula according to the invention can be obtained from suppliers of laboratory wares such as Cole-Parmer, Chicago, Ill. U.S.A. Wire suitable for the fabrication into the trochar described here in can be obtained from National Standard Company, Santa Fe Springs, Calif., U.S.A.

Figure 4:
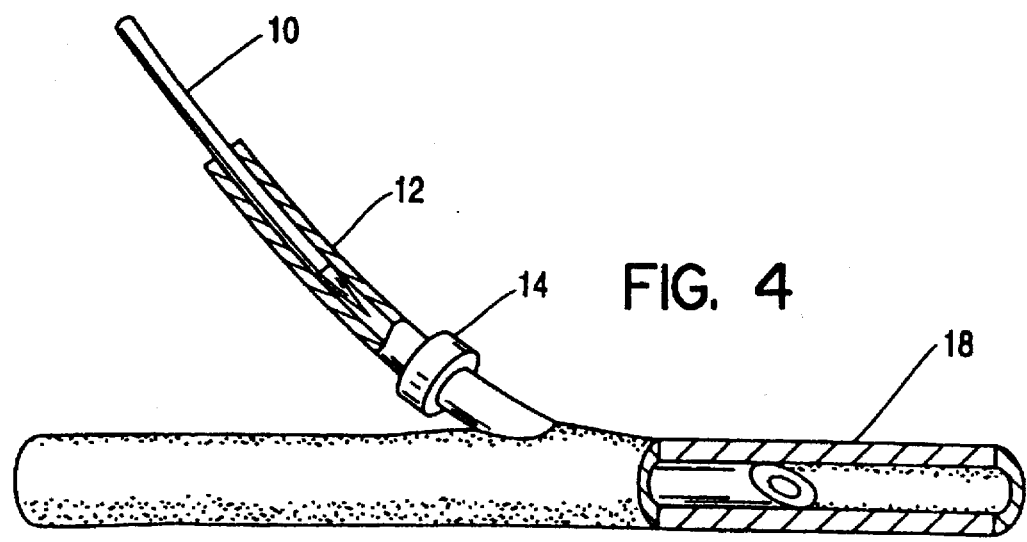
FIG. 4 shows the microcannula in place in a blood vessel or other hollow tube with the trochar in the process of being withdrawn.

When in use to cannulate a small blood vessel or hollow organ the trochar 10 and microcannula tube 12 are used as a unit (FIGS. 3–5). The trochar 10 is placed tightly fitting in the lumen of the microcannula 12 with the trochar tip 11 protruding beyond the microcannula's beveled leading edge 16. The trochar tip 11 is used to pierce the wall of the blood vessel 18. The beveled leading edge 16 of the microcannula comes into contact with the outside of the blood vessel 18 outer wall slightly displacing the wall of the blood vessel and stretching the hole punctured in the blood vessel wall. By further advancing the microcannula and trochar together, the microcannula is easily threaded through the hole into the lumen of the blood vessel.

As a result of the tight fit of the trochar and microcannula, the cannulation of small blood vessels can be accomplished without the necessity of first incising a blood vessel followed by insertion of a cannula and trochar. By using the trochar and microcannula as a unit, bleeding can be minimized and the possibility of damaging the blood vessel with an incision that is too large is eliminated.

In a second preferred embodiment, a microcannula adapted for use with fluid supply systems such as syringes and pumps is provided having a portion of the microcannula with a decreased inside diameter 23 which provides friction contact between the lumen of the microcannula and the trochar (FIG. 10). The area of decreased inside diameter 23 is formed when the microcannula end distal to the tip 25 is joined to a tube of larger diameter 21 (FIG. 7). The outside diameter of the larger tube 21 may range between 0.020 inches to 0.028 inches, and have an inside diameter of between 0.015 inches to about 0.017 inches. This friction provided by the area of decreased inside diameter 23 holds the trochar in the microcannula tube when the tip of the trochar 11 and microcannula contact, pierce and advance into the blood vessel or other hollow anatomical structure to be cannulated. The inside measurement of the area of reduced diameter 23 may vary depending on the diameter of the trochar being used, and is sufficiently reduced to provide the necessary friction to hold the trochar in place as described above. When the trochar is formed from a wire having a diameter of approximately 0.008 inches, the area of decreased inside diameter will have a diameter of approximately 0.006 inches to about 0.0075 inches. The approximate length of the decreased inside diameter 23 is about 0.25 mm to about 1.0 mm.

The area of decreased inside diameter 23 is distal to the pointed tip 11 of the trochar, wherein the distal direction is the direction away from the tip 11 of the trochar (FIG. 10). While the area of decreased inside diameter 23 is located at any point distal to the tip of the microcannula tube 12 and may be provided at any point on the length of the microcannula tube 12, it is preferred to limit the area of decreased inside diameter to a segment that would align with the approximate midpoint of the trochar 10 when the trochar is inserted within the lumen of the microcannula with the tip of the trochar extending beyond the tip of the microcannula.

In the second preferred embodiment, the area of reduced inside diameter is formed during welding of the distal end of the microcannula to a slightly larger tube of similar composition. The resulting microcannula (FIG. 10) may be used with fluid supply systems such as syringes or pumps through connection with the larger diameter tube. For example, in a specific embodiment, the microcannula tube 12 is welded to a small angiocath and the resulting unit attached to peristaltic pump tubing by leur connectors.

In order to weld small perfluorocarbon or other biocompatible polymer tubes commonly used in medical catheters, a radio-frequency welding apparatus is employed (SEBRA Engineering, Tucson, Ariz.). In the second embodiment, the friction contact between the trochar and the inner walls of the lumen of the microcannula is provided by an area of reduced diameter at the site of the weld, e.g., at the site of joinder 23 between the smaller 12 and larger 21 tubes. The friction provided by the area of reduced diameter at the site of the weld joint holds the trochar immobilized in the microcannula tube when the tip of the trochar and microcannula contact, pierce, and advance into the blood vessel being cannulated. Besides providing a microcannula adapted for use with fluid supply systems such as syringes and pumps, an important advantage provided by this embodiment over the prior art is that the area of reduced diameter of the microcannula is distal to the tip and does not interfere with the structural integrity of the tip.

Generally, the microcannula of the invention is produced by aligning the distal end of a small bore tube with a slightly larger diameter tube such that the tubes overlap slightly, then applying means of permanently fixing the two tubes together. Preferably, the tubes are joined together by applying sufficient heat and pressure to form a weld between the tubes at the site of overlap such that the inside diameter of the small bore tube is sufficiently reduced to hold the solid trochar removably in place.

More specifically, the microcannula adapted for use with fluid supply systems and having an area of reduced inside diameter distal to the tip which removably holds the trochar in place is made by the process shown in FIGS. 7–10. A smaller diameter tube and a larger tube are aligned on a mandrel 27, as shown in FIG. 7. The smaller tube 12 is aligned with the larger tube 21 such that the tubes overlap by about 0.5 mm to about 1.5 mm, preferably about 1 mm (about ½₃₂"). The aligned tubes and mandrel are fitted into a welding die 22 (FIG. 8). A weld is formed by applying sufficient heat and pressure at the site of overlap to effectively weld the two tubes to each other and produce an area of reduced inside diameter. In a preferred embodiment, a temperature ranging from about 390° C. to about 410° C. and a pressure of about 1–4 psi are applied for approximately 15–25 sec to the tube-mandrel unit in the die at the site of tube overlap. More preferably a temperature ranging from about 392° C. to about 402° C. is applied for 20 sec at a pressure of about 2 psi. The microcannula is allowed to cool and removed from the mandrel for inspection of physical integrity and trochar fit. The finished microcannula has an area of reduced inside diameter 23 at the weld site as shown in FIG. 10 of approximately 0.25–1.0 mm and the inside diameter of the reduced area is approximately 0.007 inches. The area of reduced diameter 23 provides sufficient friction to keep the trochar in place, and offers the advantage of eliminating one step (the swedging step) in the manufacturing process when the cannula is attached at its distal end to an appropriate section of larger tubing. Further, in contrast to prior art cannulas, the microcannula shown in FIG. 10 having a reduced inside diameter distal to the tip preserves the integrity and shape of the proximal end of the microcannula.

What is claimed is:

1. A microcannula, comprising:
    a first hollow tube having a beveled tip; wherein said tube has a segment distal to the tip having an expanded outside diameter;
    a second hollow tube joined to said first hollow tube at a point distal to the tip of said first tube;
    an area of reduced inside diameter at said point of joinder; and
    a solid conically pointed trochar tightly but removably fitted in the lumen of said first tube, said trochar sufficiently long to protrude beyond the leading edge of said beveled tip, wherein said trochar is removably immobilized by friction contact provided at said area of reduced inside diameter.

2. The microcannula of claim 1, wherein said first tube has a cross sectional size smaller than a 24 gauge needle and a larger than a 29 gauge needle.

3. The microcannula of claim 1, wherein said beveled tip has an angle of about 25°±0.5°.

4. The microcannula of claim 1, wherein said area of reduced inside diameter providing friction contact with said trochar is about 0.25 mm to about 1.00 mm in length.

5. The microcannula of claim 1, wherein said diameter of said area of reduced inside diameter is about 0.006 inches to about 0.0075 inches.

6. The microcannula of claim 1, wherein the outside diameter of said first tube is about 0.016 inches.

7. The microcannula of claim 1, wherein the inside diameter of said first tube is about 0.008 inches.

8. The microcannula of claim 1, wherein the walls of said tube are a biocompatible polymer.

9. The microcannula of claim 1, wherein said first and second tubes are joined by a weld.

10. The microcannula of claim 1, wherein the expanded outside diameter of said segment is provided by a ring around the outside of said tube.

11. The microcannula of claim 10, wherein said ring is tightly fitted on said first tube but may be moved thereon.

12. The microcannula of claim 11, wherein said ring and said outside of said first tube are in an interference fit with respect to one another.

* * * * *